(12) United States Patent
Ortiz et al.

(10) Patent No.: US 8,916,107 B2
(45) Date of Patent: Dec. 23, 2014

(54) PORTABLE DECONTAMINATION AND DEODORIZATION SYSTEMS

(76) Inventors: Luis M. Ortiz, Albuquerque, NM (US); Anthony Michael Baca, Albuquerque, NM (US)

( * ) Notice: Subject to any disclaimer, the term of this patent is extended or adjusted under 35 U.S.C. 154(b) by 806 days.

(21) Appl. No.: 12/632,692

(22) Filed: Dec. 7, 2009

(65) Prior Publication Data

US 2010/0143204 A1      Jun. 10, 2010

Related U.S. Application Data

(60) Provisional application No. 61/120,471, filed on Dec. 7, 2008, provisional application No. 61/152,812, filed on Feb. 16, 2009.

(51) Int. Cl.
*A61L 9/14* (2006.01)
*A61L 2/22* (2006.01)

(52) U.S. Cl.
CPC .............. *A61L 9/14* (2013.01); *A61L 2209/11* (2013.01); *A61L 2209/111* (2013.01); *A61L 2/22* (2013.01); *A61L 2202/25* (2013.01)
USPC .................................. 422/292; 422/5; 422/28

(58) Field of Classification Search
CPC ... A61L 9/14; A61L 2202/16; A61L 2202/25; A01M 7/005; A01M 7/0057; B05B 15/10
USPC ........................................ 422/5, 28, 292, 300
See application file for complete search history.

(56) References Cited

U.S. PATENT DOCUMENTS

| | | | | | |
|---|---|---|---|---|---|
| 3,567,125 | A | * | 3/1971 | Houghton | 239/204 |
| 4,776,403 | A | * | 10/1988 | Lejosne | 169/61 |
| 4,784,324 | A | * | 11/1988 | DeWitt et al. | 239/165 |
| 2005/0112022 | A1 | * | 5/2005 | Morgan | 422/292 |
| 2008/0038166 | A1 | * | 2/2008 | Hill et al. | 422/292 |

* cited by examiner

*Primary Examiner* — Timothy Cleveland
(74) *Attorney, Agent, or Firm* — Luis M Ortiz; Ortiz & Lopez, PLLC (57) ABSTRACT

Portable decontamination and deodorization systems configured to decontaminate a target environment for specified periods of time. A housing contains pressurized media. A spherical media diffuser can be connected to and controlled by a sphere retainer module and a funnel-like orifice can be located under a lower hemisphere of the spherical media diffuser to move the spherical media diffuser and over the funnel-like orifice creating a gap there-between to evenly distribute chemical in a fog or spray throughout a room. a valve controller can be coupled by tubing between media contained in said housing and the gap formed between the spherical media diffuser and funnel-like orifice.

18 Claims, 7 Drawing Sheets

PORTABLE DECONTAMINATION AND DEODORIZATION SYSTEMS

INVENTION PRIORITY

The present invention claim priority as a continuation application to provisional patent application Ser. No. 61/120,471, which was filed Dec. 7, 2008 and also as a continuation to provisional patent application Ser. No. 61/152,812, which was filed Feb. 16, 2009. Both provisional applications are herein incorporated by reference.

FIELD OF THE INVENTION

The present invention is generally related to decontamination and sterilization systems and equipment for use to treat enclosed environments (e.g., rooms in a hospital, rooms in schools and nurseries, business environments, hotels and lodging facilities, fitness facilities, homes). The present invention is also related to system that can be used to deodorize an environment as part of or independently of decontamination procedures. The present invention is particularly related to a portable decontamination and deodorization systems.

BACKGROUND

There is increasing evidence implicating hospital environments in the spread of nosocomial pathogens. Eradicating these organisms from hospital equipment, rooms and wards is essential as more citizens are becoming infected even during only routine examinations and procedures. Sanitizing surfaces is an often overlooked yet critical component of breaking the cycle of infection in health care environments. What is needed are portable and also multi-level decontamination and deodorization system as proposed herein by the present inventors.

The present inventors have determined that vapor spreading technology as described herein ensures three dimensional distribution of treatment media (e.g., chemicals) and rapid deactivation of nosocomial pathogens, including: MRSA, Norovirus, *Clostridium, Difficile, Serratia, Acinetobacter, Aspergillus, Klebsiella, Enterobacter*, VRE, Gram-negative rods.

Treatment of hospitals and medical facilities using the present invention to bio-decontaminate its specialist beds and other hard-to-clean medical devices can reduce equipment cleaning costs and asset down-time. Ideally, a facility's own staff should be able to decontaminate rooms or equipment using the present invention.

In order to overcome shortfalls in the current art, the present inventors describe a portable, state-of-the-art system that can be by stretched infection control departments and personnel attempting to combat dangerous bacteria and viruses and reduce infection and the spread of disease. Hospitals are not the only benefactor of the present technology given that infection has been widely reported to have occurred/originated from school gymnasiums, fitness facilities, nursing homes, day cars, commercial passenger vehicles (e.g., airplanes, cruise ships) and the like.

SUMMARY OF THE INVENTION

Portable decontamination and deodorization systems are disclosed including a spherical outlet that enables 360 degree coverage with treatment media (e.g., chemicals or biodegradable fluid) within a room or other closed environments.

A portable, multilevel decontamination and deodorization system is also disclosed.

In accordance with features of the present invention, a portable decontamination unit can be used to treat an environment at various vertical levels within an enclosed environment (e.g., hospital room).

In accordance with features of the present invention, a decontamination unit can be used to deodorize an environment at various vertical levels as part of or independently from known decontamination procedures.

In accordance with features of the present invention, a decontamination system can be provided in a two-part system: a decontamination station, and a programming and status station.

In accordance with additional features of the present inventions, the decontamination station can include telescoping media delivery assembly with a spherical diffuser located at the end of the telescoping tubing. The spherical media diffuser in combination with a funnel base can be configured to evenly distribute treatment media in a fog horizontally throughout a room as the telescoping tubing is moved electromechanically upward from the base of the decontamination station to a defined limit above the base.

In accordance with features of the present inventions, the base of the decontamination station can include an electromechanical module for controlling and causing movement of telescoping chemical delivery tubing and a spherical media diffuser located at the end of the telescoping tubing, upward from the base. The spherical media diffuser in combination with a funnel-like orifice located beneath the lower hemisphere of the spherical media diffuser can be configured to evenly distribute treatment media in a fog horizontally throughout a room as the telescoping moves upward from the base of the decontamination station to a defined limit above the base.

In accordance with other features of the present inventions, the base can include a treatment vessel, an air pressure vessel, a rechargeable power source, valve controller coupled to each of the chemical and pressure vessel to control the flow of each into the telescoping tubing, a microprocessor to control the valve controller and electromechanical module.

In accordance with additional features of the present inventions, the base can include environmental sensors to monitor an environment and wireless communications to enable communication between the decontamination station and the programming and status station.

In accordance with another feature of the present inventions, the decontamination station acting as a base can include a data connector to establish direct communication between the decontamination station and a data connector on the programming and status station that is complimentary to the data connector on the base when they are assembled together prior to operation when a two part system is provided.

In accordance with additional features of the present inventions, the decontamination station serving as a base can be self-contained during operation and can include a rechargeable power source that provides power to the system during operation, but can be recharged by connection to 110 vac power supply when not in use. It can be appreciated that direct electrical connection during operations to 110 vac is also possible, but may be less desirable in the treatment area; especially given the portability desires for a more robust system. Furthermore, the programming and status station would ideally include a rechargeable power source to enable its operation and placement outside of the door of the treatment area where utility power may not be available without creating a hazard along the floor (e.g., hallways in a hospital should remain power cord free to prevent tripping of staff and patients walking along a hallway).

In accordance with additional features of the present inventions, the programming and status station can be placed outside of the door of a treatment area and provide visual warnings about ongoing treatment, and block entry to a room undergoing decontamination treatment. An operator of the system can also control and communicate with the treatment station inside the room, e.g., to take sensor readings, modify treatment procedures, etc. Furthermore, a safety "shut off" button can be used to interrupt treatment procedures if entry into the treatment area becomes necessary.

DETAILED DESCRIPTION

Figure 1:
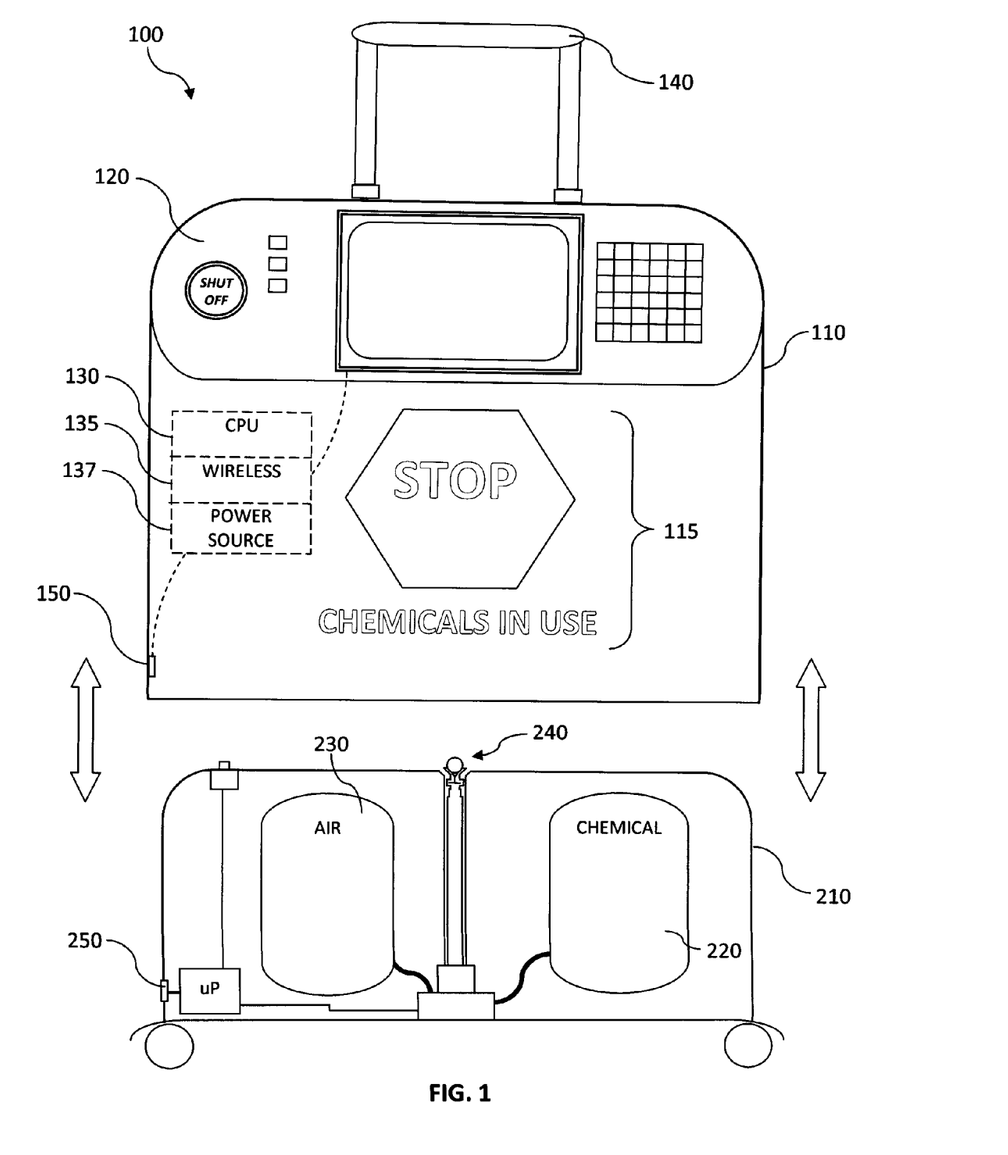
FIG. 1 illustrates a front view of a portable, multilevel decontamination and deodorization system provided in a two part system: including a decontamination station, and a programming and status station.

Referring to FIG. 1, illustrated a front view of a portable, multilevel decontamination and deodorization system 100 provided in a two part system: including a decontamination station 210 and a programming and status station 110. The present system can be used to distribute treatment media such as chemicals and biodegradable treatments in fluid or power form. The treatment media is delivered by the present system to decontaminate and/or deodorize an environment at various levels as part of or independently of decontamination procedures. It should be appreciated that although a two part system is described herein, only the treatment station 210 alone can be used to accomplish the task of decontamination and deodorization. The programming and status station 110, however, is what makes the present invention even more robust to enterprises interested in an effective treatment program. The disclosure of a two-part system herein is not meant to limit the scope of the present invention and the scope should be determined broadly in light of the appended claims.

The decontamination station 210 includes a media deliver assembly 240, which can include telescoping hardware and capabilities. The decontamination station 210 contains a compressed air vessel 220 and chemical vessel 230. The compressed air vessel 220 can be provided in the form of a highly pressurized compressed air tank. It should also be appreciated that the compressed air vessel can be provided in the form of an electromechanical air compressor. The chemical vessel can be provided in the form of a refillable reservoir, or can be provided in the form of factory filled tanks. Other means of provided chemical can be accommodated in the present invention. It is envisaged that the chemical is delivered in a wet form from the media delivery assembly 240; however, a power based chemical can also be delivered with the assistance of air pressure. Most environments would benefit mostly from a wet fog or spray delivered form the present system. A warm fog would also move throughout a room and reach hard to reach areas (e.g., underneath a bed frame in a hospital).

The decontamination station 210 serves as the base for the programming and status station 110 when the two are assembled for storage and charging (where applicable). The decontamination station 210 can include a data connector 250 to establish direct electrical communication the programming and status station 110 which can includes a data connector 150 that is complimentary to data connector 250. When the two stations are assembled together prior to operation, the data connector 250 and complimentary data connector 150 enable the stations to operate without wireless communication. The connection can also enable the programming and status station to become recharged when it is placed onto the chemical delivery assembly 210, which then serves as the programming and status station's base.

The programming and status station 110, when provided, includes a control panel 130 to enable programming control over the decontamination station 210. At the control panel, a user can specify the size of the room that is being treated, duration of treatment, spray/fog pattern desired, etc. The microprocessor (CPU) 133 can included access to embedded programming that will enable/assist a user to determine the most effective treatment routine for the specified room or type of environment. Industry-specified standards can be established that prescribe treatment, requirement/suggestions, which can be provided as part of the programming and database that can be provided as part of the overall system. A wireless module 135 can enable access to data networks to download updates or access remote information, including establishing communication with the decontamination station 210 during operations. Wireless module can include WiFi (802.xx) access, Bluetooth, and telecommunications network access (e.g., CDMA, 3G, GSM, GPRS, TDMA, SMS, etc.). A rechargeable power source 137 provides power to the programming and status station 110 and is recharged by the decontamination station 210 when the two are assembled and stored.

Written indicia such as labels and warnings 115 can be provided on the front surface of the programming and status station 110 in order to indicate to people passing by or wanting entry into the room when placed in front of a door entry into the treatment environment that treatment with chemicals is in progress. A telescoping handle 140, similar in operation to the type provided with modern luggage, enables an operator to easily move the system 100 from storage to places of use.

Figure 2:
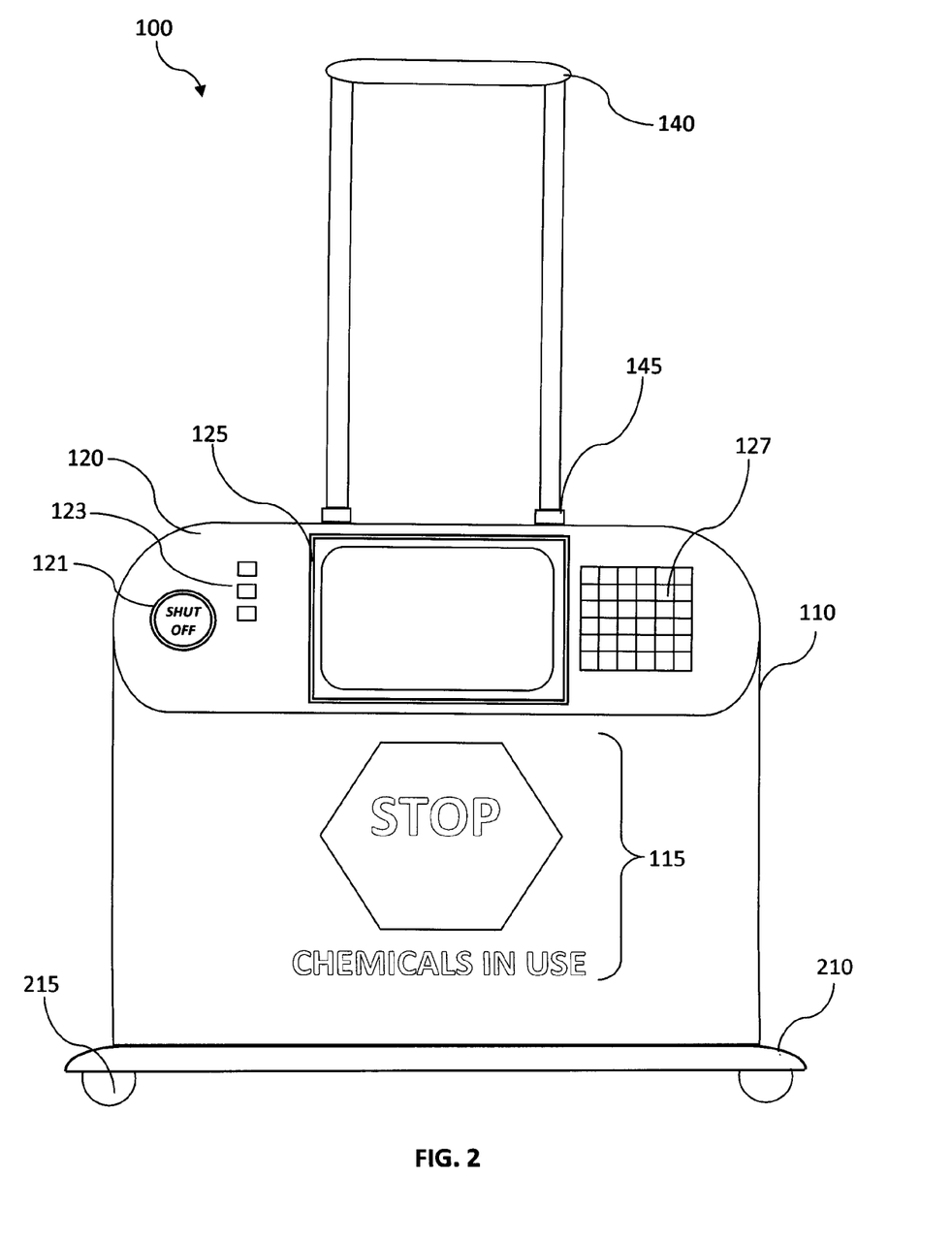
FIG. 2 illustrates a front view of the two part portable, multilevel decontamination and deodorization system illustrated in FIG. 1, assembled with the programming and status station covering and attached to the decontamination station and illustrated the major components visible at the exterior of the programming and status station.

Referring to FIG. 2, wheels 215 are provided at the bottom of decontamination station 210 in order to facilitate movement of the system 100 by operators. The telescoping handle 140 is shown in an upright deployed position from its base 145. A protective flaring 210 can be provided to prevent chemical from covering the wheels and to facilitate cleaning of the system 100 after use.

At the control panel 120, an emergency shut-off button 121 can be provided that can enable anyone to terminate procedures. The button can be illuminated and include a bright red lens to further indicate warning and the existence of a potential hazard. Additional buttons or status lights 123 can be provided on the control panel 120. A display screen 125 (e.g., flat panel) can provide a user with a graphical user interface to enhance programming and operational features. A keypad 127 can enable additional data entry into the system 100. It can be appreciated that the display screen can be provided as a touch-sensitive display to also enable control and user interface with the system 100.

Figure 3:
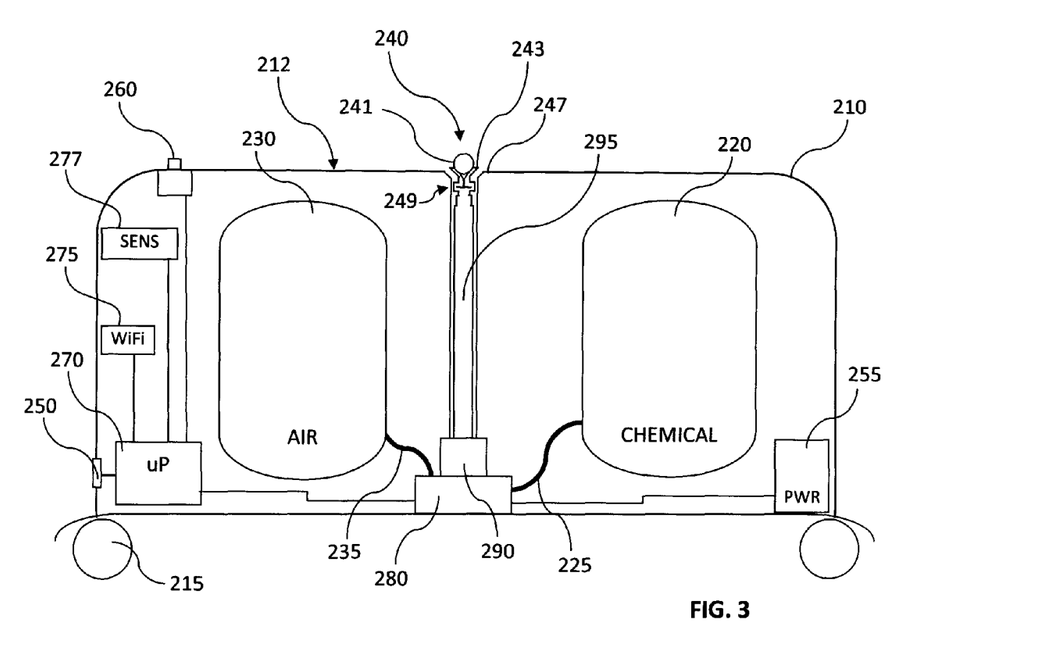
FIG. 3 illustrates a cross-section front view of a portable, multilevel decontamination and deodorization system, such a illustrated in FIG. 1, with modules contained therein also illustrated.

Referring to FIG. 3, additional details for a decontamination station 210 are illustrated. A decontamination station 210 can include a telescoping chemical delivery assembly 240 with a spherical media diffuser 241 located at the end of telescoping tubing 295. An orifice 243 that can be provided in the form of a funnel-like base for the spherical diffuser 241 and can be configured to distribute chemical as specified by the user (e.g., based on programming), such as in a fog or spray spread mostly horizontally throughout a room as the telescoping tubing 295 is moved electromechanically by an electromechanical module 290 upward from the top surface 112 of the decontamination station 110 to a defined limit above the top surface 112. The spherical media diffuser 241 can be adjustably secured at its position on the end of the telescoping tubing 295 by a spring loaded retainer module 249, which enables gas to pass around and through the spring loaded retainer module 249 to the spherical media diffuser 241. The spring loaded retainer module can enable the spherical media diffuser 241 to move upward (open the gap between it and the orifice 243) as gas pressure is increased. Alternatively, the spring loaded retainer module 249 can be computer controlled in order to control the spherical media diffuser's 241 movement and its ability to open (create a gap) relative to the orifice 243. A computer controlled retainer module can also provide more control over fogging/spraying patterns.

The electromechanical module 290 is ideally computer-controlled to cause movement of telescoping chemical delivery tubing and a spherical diffuser located at the end of the telescoping tubing, upward from the top surface 112. The spherical diffuser in combination with a funnel-like orifice located beneath the lower hemisphere of the spherical diffuser are configured to evenly distribute chemical in a fog horizontally throughout a room as the telescoping moves upward from the base of the decontamination station to a defined limit above the base. It can be appreciated that a simpler system can be devised based on the teaching herein where the system is turned on with a delay timer and the electromechanical module 290 gradually deploys the telescoping tubing 295 over a defined period of time to dispense the chemical treatment. Nowadays, however, a computer-controlled system is more desirable. Where simpler use is desired, an on/off button 260 can be provided to initiate and terminate treatment. The button 260 can also be provided for other functions (e.g., emergency shut off) where a system is computer controlled.

A valve controller 280 is provided that is coupled by tubing 225, 235 to each of the chemical vessel 220 and air pressure vessel 230, and controls the flow of each into the telescoping tubing 295. In a microprocessor-controlled system, the valve controller 280 is operational as an electromechanical system with the use of high pressure pneumatic controls and hardware, which are well developed by, and available from, industry.

In accordance with additional features of the present inventions, the base can include environmental sensors 277 to monitor environmental conditions, wireless communications 275 to enable communication between the decontamination station 210 and the programming and status station 110.

The decontamination station 210 can be self-contained during operation and can therefore include a rechargeable power source 255 that provides power to the system during operation, but can be recharged by connection to 110 vac power supply when not in use. It should be appreciated that direct electrical connection during operations to 110 vac is also possible, but may be less desirable in the treatment area; especially given the portability desires for a more robust system. Furthermore, the programming and status station ideally includes a rechargeable power source to enable its operation and placement outside of the door of the treatment area where utility power may not be available without creating a hazard along the floor (e.g., hallways in a hospital should remain power cord free to prevent tripping of staff and patients walking along a hallway).

Figure 4:
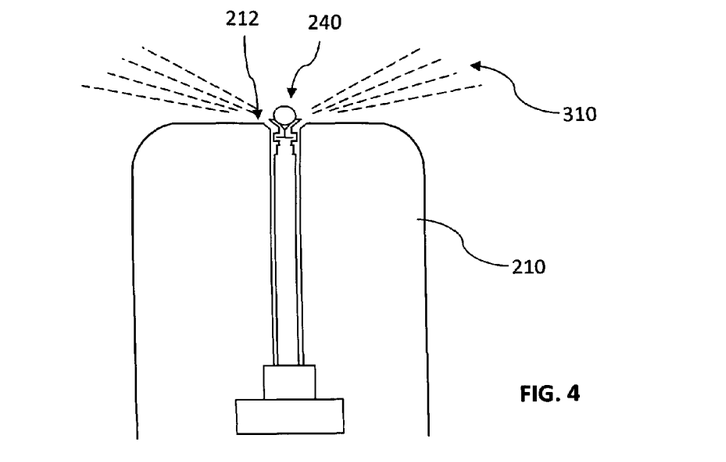
FIG. 4 illustrates a front view of a portable, multilevel decontamination and deodorization system at operation in a first level of operation, fogging/spraying chemical mostly horizontally throughout an environment (not shown).
Figures 5, 6:
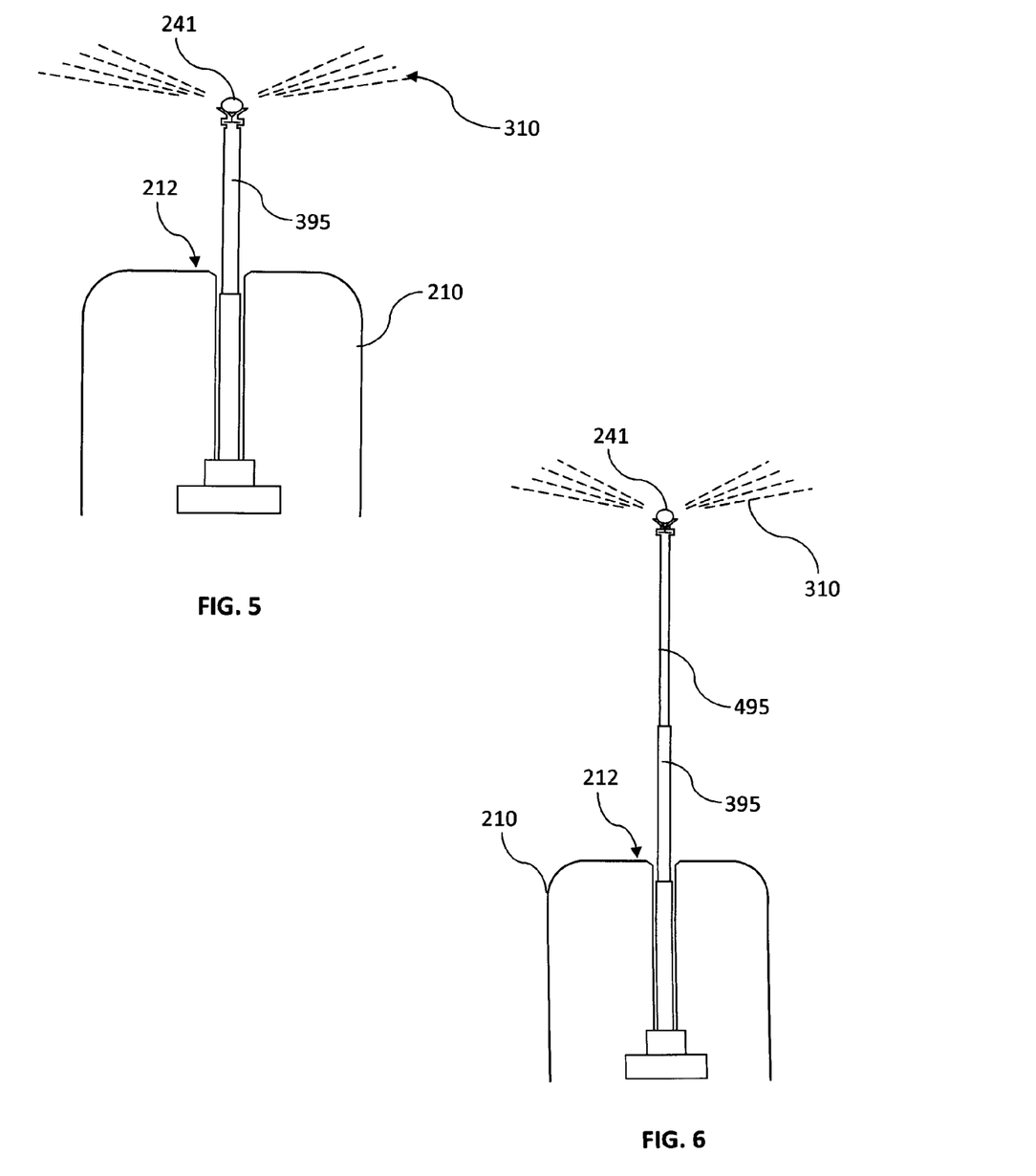
FIG. 5 illustrates a front view of a portable, multilevel decontamination and deodorization system at operation in a second level of operation, fogging/spraying chemical mostly horizontally throughout an environment (not shown).
FIG. 6 illustrates a front view of a portable, multilevel decontamination and deodorization system at operation in a second level of operation, fogging/spraying chemical mostly horizontally throughout an environment (not shown).

Referring to FIG. 4, illustrated is a perspective view of a decontamination station 210 with the telescoping chemical delivery assembly 240 distributing chemical treatment 310 from an initial deployment at the surface 212 of the decontamination station 210. Ideally, the initial level of operation begins at a level low enough to the ground to enable chemical to spread underneath room furnishing (e.g., hospital bed frames). The initial level can begin at about 10-14 inches while still accommodating the chemical vessel 210 and other components within the decontamination station 210. FIG. 5 illustrates a perspective view of a decontamination station 210 with the telescoping chemical delivery assembly 240 distributing chemical treatment 310 from a deployment level above the surface 212 of the decontamination station 210. Tubing extensions 395 is shown as the telescoping tubing is extended upward from surface 212. FIG. 6 illustrates a perspective view of a decontamination station 210 with the telescoping chemical delivery assembly 240 distributing chemical treatment 330 from a fully extended deployment level at the surface 212 of the decontamination station 210. Tubing extensions 495 is shown as the telescoping tubing is extended upward from surface 212. Additional levels of extension are possible, depending on the size of the room and capability of the designed unit in accordance with these teachings.

Figure 7:
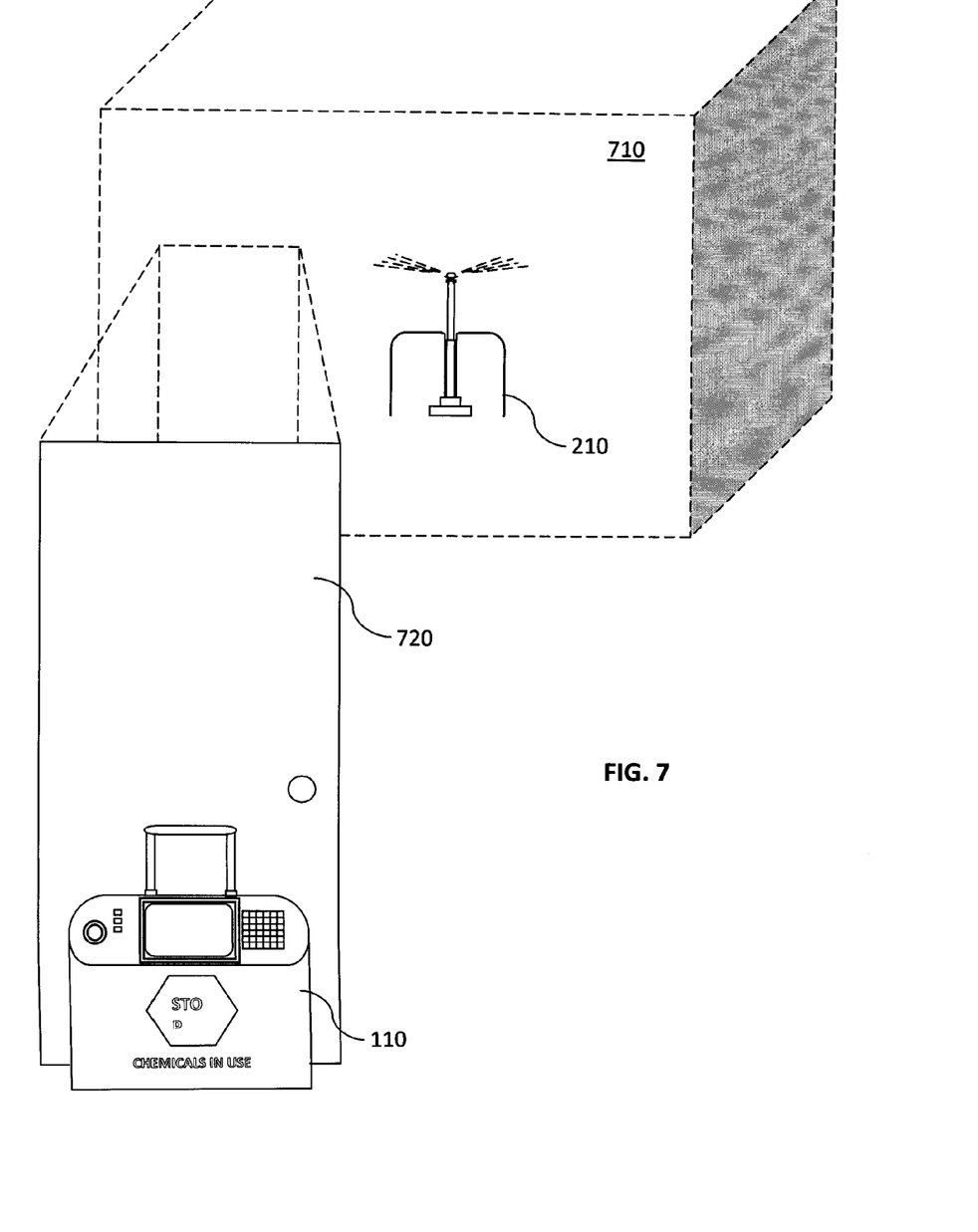
FIG. 7 illustrates the decontamination stations of the portable, multilevel decontamination and deodorization system located within a room where treatment operations are ongoing and a programming and status station located outside the door to the room being treated to warn against/block entry to the room.

Referring to FIG. 7, in accordance with additional features of the present inventions, the programming and status station 110 can be placed outside of the door 720 leading into a treatment area illustrated as a room 710 and provide visual warnings about ongoing treatment, and block entry to the room 710. An operator of the system can also control and communicate with the treatment station 210 located inside the room 710, e.g., to take sensor readings, modify treatment procedures, etc. Furthermore, a safety "shut off" button can be used to interrupt treatment procedures if entry into the treatment area becomes necessary.

Figure 8:
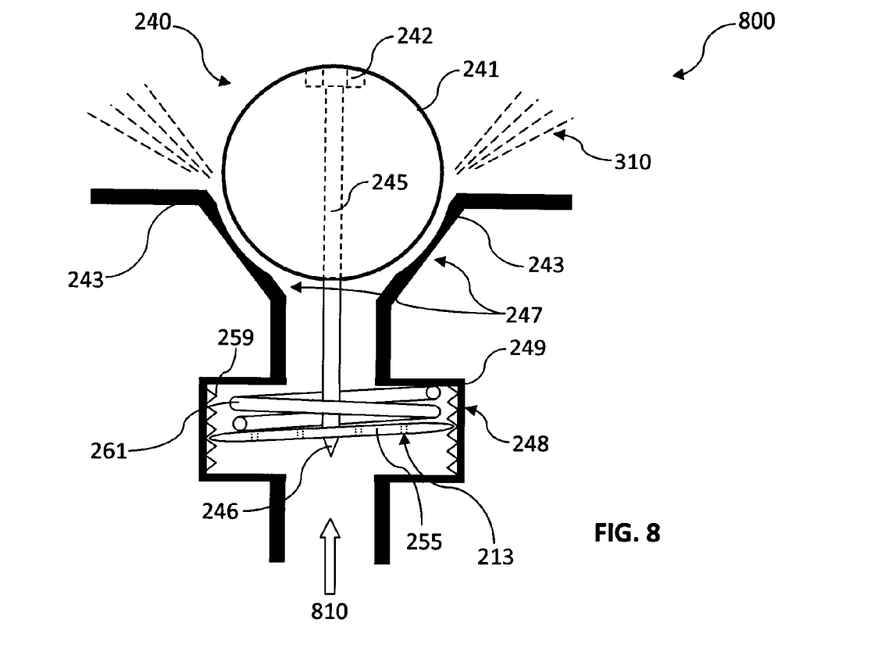
FIG. 8 illustrates a side cross-section view of a spherical media delivery outlet that can be used in a portable system to enable broad, 360 degree spraying/fogging of chemical or treatments from a decontamination and deodorization system within which the spherical delivery outlet is used.

In accordance with features of the present inventions, a side view 800 of a spherical delivery outlet 212 including a spherical media diffuser 241 and supporting hardware that can be used in portable decontamination and deodorization stations is shown in more detail in FIG. 8. FIG. 8 illustrates a side cross-section view of a spherical media delivery outlet that can be used in a portable system to enable broad, 360 degree spraying/fogging of chemical or treatments from a decontamination and deodorization system within which the spherical delivery outlet is used.

At the spherical delivery outlet 212 is a spherical media diffuser 241 position over a geometrically conforming orifice 243. A hex adjustment 242 located at the top of the spherical media outlet 241 includes an adjustment shaft 245 connectable within a sphere control module 249 to a perforated control disk 255. The perforated control disk 255 can interface with adjustment threading 259 formed within the sphere retainer module 249 to enable adjustment of the spherical media diffuser 241 over the orifice 243. A spring 261 can provide pressure against the perforated control disk 255 and an upper wall of the sphere control module 249. Adjustment of the hex adjustment 242 creates a media escape gap 247 of varying width. The width of the media escape gap 247 will determine the size particles or droplets emitted from between the spherical media diffuser and the orifice 243. The width of the media escape gap 247 will also determine whether the media is emitted as a fog or a spray. It should be appreciated that the sphere control module 247 can also be provided in the form of an electromechanical module such as that discussed previously. A more elaborate sphere control module can be computer controlled with sensor feedback to control the size of the media escape gap 247. A cone-shaped nut 246 can be mounted at the bottom surface of the perforated control disk and secure the adjustment shaft 245. Being cone shaped, the nut can help direct media towards perforations on the perforated control disk 255.

Figure 9:
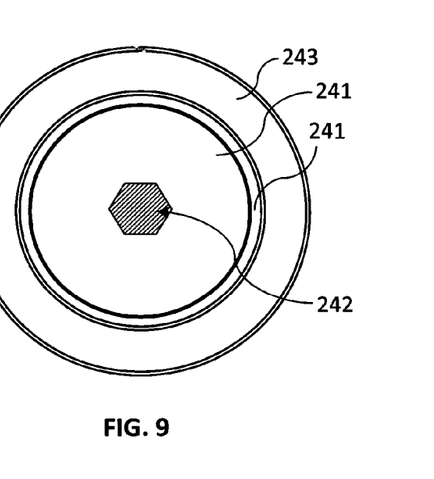
FIG. 9 illustrates a top view of a sphere emplaced over an orifice, the sphere having an adjustable hex screw.
Figure 10:
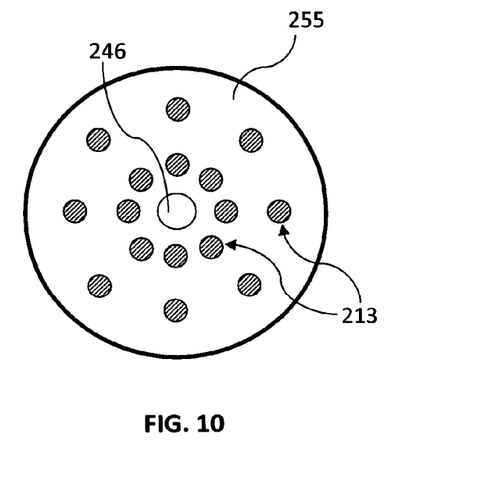
FIG. 10 illustrates a top view of adjustment baffle disk used to enable adjustment and control over the sphere during set up and operation.

FIG. 9 illustrates a top view of a spherical media diffuser 241 that would be emplaced over an orifice 243. FIG. 10 shows the sphere 241 having an adjustable hex screw 242 at the top of the sphere. FIG. 10 illustrates a top view of adjustment baffle disk 255 used to enable adjustment and control over the sphere 241 during set up and operation. The sphere is perforated 213 sufficient to allow media to flow there through.

Figure 11:
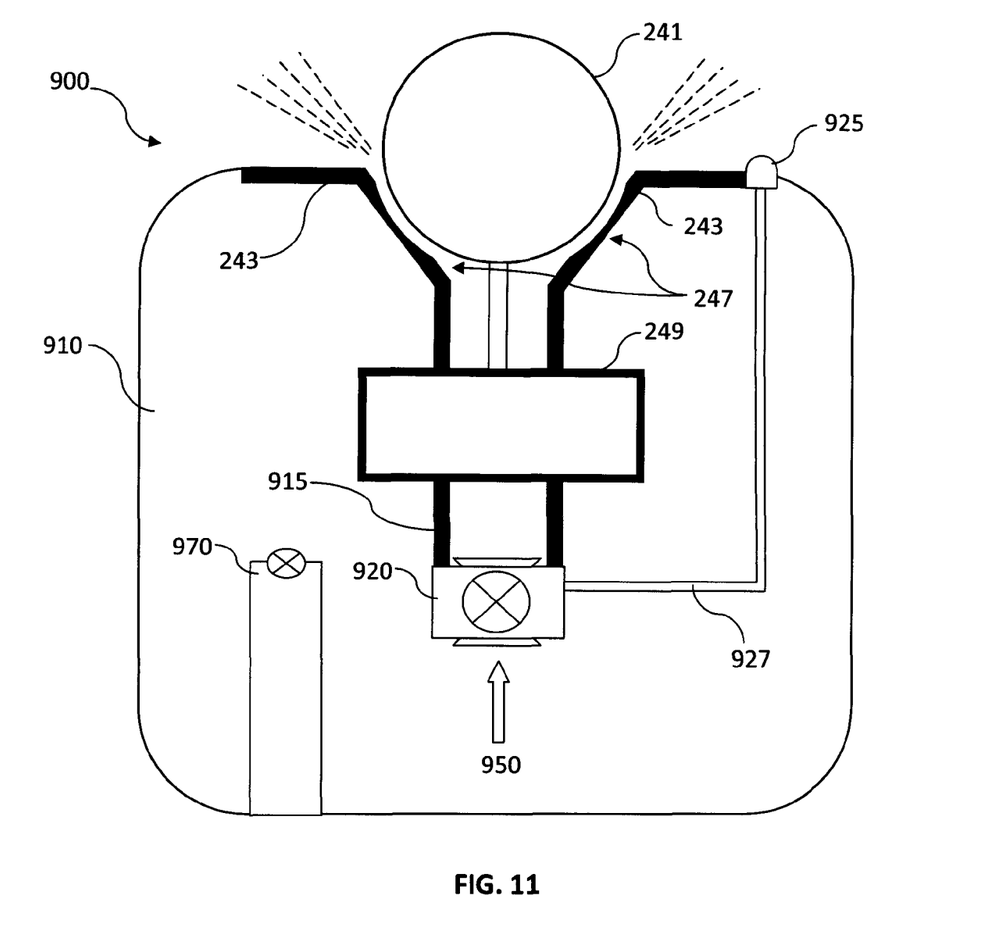
FIG. 11 illustrates a side view of a portable, decontamination and deodorization system for fogging/spraying operations as an alternative embodiment.

FIG. 11 illustrates a side view of a portable, decontamination and deodorization system 900 for fogging/spraying operations as an alternative embodiment. In applications where, although portable, a system as described with respect to FIGS. 1-7 is still too large for use, a more portable (e.g., handheld) delivery means can be provided. Similar to an aerosol canister, the portable, decontamination and deodorization system 900 can contain media in a housing 910. A valve controller 920 can enable media 950 to flow from inside the housing 910 through tubing 915 past the gap 247 created between the spherical media diffuser 241 and the orifice 243. The valve can be actuated by a switch 925. The switch 927 can be electrical or mechanical with a connection 927 to the valve controller 920 that can be either electrical or mechanical. If mechanical, the switch can be pressed down to actuate the valve controller 920. An electrical switch requires that the controller valve also be electromechanical. The electrical switch can also be in the form of an infrared, RFId or timer actuated module for remote activation, which may be necessary to ensure safety to personnel during operation. Details of the sphere control module 249 are not shown in FIG. 11 because it should be appreciated based on all of the teaching herein that the sphere control module can also be electromechanical (e.g., pneumatically controlled) rather than purely mechanical. Also shown in FIG. 11 is a pressurization module 970. The pressurization module 970 creates the pressure needed to force delivery of the media through the portable, decontamination and deodorization system 900. The pressurization module 970 can be provided in the form of an interface for receiving disposable $C_02$ cartridges, or as an adapter to receive gas pressurization from an external source (e.g., a recharge interface). Media can also be inserted through the pressurization module 970 as an interface for recharging the housing 910

The invention claimed is:

1. A self-contained portable, multilevel decontamination and deodorization system restricted for use inside a room inside a building and capable of decontaminating and deodorizing the room at various levels within the overall height of the room starting from at least ten inches above ground level within the room to reach areas beneath furnishings that may exist in the room and reaching a defined limit above ground level within the room to reach above the furnishings that may exist in the room, comprising:

a decontamination station having an upper, outer surface standing about ten inches from the ground during initial operation and including a compartment configured to contain chemical vessel, air pressure vessel, and telescoping chemical delivery tubing connected to the chemical and air pressure vessels and including a spherical media diffuser at its end, wherein the portable, multilevel decontamination and deodorization system is configured with the telescoping chemical delivery tubing to decontaminate a target environment at more than two vertical levels beginning from at least ten inches above the ground and reaching to a defined limit above ground level over a defined duration of time;

an electromechanical module configured to control and cause movement of telescoping chemical delivery tubing and a spherical media diffuser located at the end of the telescoping tubing, upward and downward from the upper, outer surface, wherein operation of said electromechanical module is controlled by a microprocessor; and a valve controller coupled to each of the chemical and pressure vessel to control flow of each into the telescoping chemical delivery tubing, wherein operation of said valve controller is controlled by the microprocessor.

2. The portable, multilevel decontamination and deodorization system of claim 1, further comprising a funnel-like orifice located beneath a lower hemisphere of the spherical media diffuser and configured to evenly distribute chemical in a fog mostly horizontally throughout a room.

3. The portable, multilevel decontamination and deodorization system of claim 1, further comprising a funnel-like orifice located beneath a lower hemisphere of the spherical media diffuser and configured to evenly distribute chemical in a fog mostly horizontally throughout a room as the telescoping chemical delivery tubing moves upward from the upper, outer surface of the decontamination station to a specified limit above the base.

4. The portable, multilevel decontamination and deodorization system of claim 1, further comprising a programming and status station including a programming and status station microprocessor managing a control panel and communications module, wherein the control panel enables a user to set up and remotely operate the decontamination station and the communications module enables remote monitoring of the decontamination station from outside a treatment area.

5. The portable, multilevel decontamination and deodorization system of claim 1, further comprising environmental sensors configured to enable monitoring of treated environments.

6. The portable, multilevel decontamination and deodorization system of claim 4, said decontamination station comprising wireless communications to enable communication between the decontamination station and a remote programming and status station.

7. The portable, multilevel decontamination and deodorization system of claim 4, wherein said the programming and status station includes a rechargeable power source and electrical power and data connection to the environmental station during storage, said rechargeable power source configured to enable its operation and placement outside of the door of the treatment area.

8. The portable, multilevel decontamination and deodorization system of claim 4, wherein the programming and status station is configured with warning indicia and lights and is further configured for placement outside a door of a treatment area to provide visual warnings about ongoing treatment and block entry to the treatment room.

9. The portable, multilevel decontamination and deodorization system of claim 8, said programming and status station and decontamination station each further comprising wireless communications to enable communication between the decontamination station and the programming and status station.

10. A self-contained portable, multilevel decontamination and deodorization system restricted for use inside a room inside a building and capable of decontaminating and deodorizing the room at various levels within the overall height of the room starting from at least ten inches above ground level within the room to reach areas beneath furnishings that may exist in the room and reaching a defined limit above ground level within the room to reach above the furnishings that may exist in the room, comprising:
  a decontamination station having an upper, outer surface standing ten inches from the ground during initial operation and including a compartment configured to contain chemical vessel, air pressure vessel, and telescoping chemical delivery tubing connected to the chemical and air pressure vessels and including a media diffuser at its end, wherein the portable, multilevel decontamination and deodorization system is configured with the telescoping chemical delivery tubing to decontaminate a target environment at more than two vertical levels beginning from at least ten inches above the ground and reaching to a defined limit above ground level over a defined duration of time;
  an electromechanical module configured to control and cause movement of telescoping chemical delivery tubing and a media diffuser located at the end of the telescoping tubing, upward and downward from the upper, outer surface, wherein operation of said electromechanical module is controlled by a microprocessor;
  a valve controller coupled to each of the chemical and pressure vessel to control flow of each into the telescoping chemical delivery tubing, wherein operation of said valve controller is controlled by the microprocessor;
  environmental sensors configured to enable monitoring of treated environments; and
  wireless communications to enable communication between the decontamination station and a remote programming and status station.

11. The portable, multilevel decontamination and deodorization system of claim 10, wherein said media diffuser is a spherical media diffuser and the portable, multilevel decontamination and deodorization system further comprises a funnel-like orifice located beneath a lower hemisphere of the spherical media diffuser and configured to evenly distribute chemical in a fog mostly horizontally throughout a room as the telescoping chemical delivery tubing moves upward from the upper, outer surface of the decontamination station to a specified limit above the base.

12. The portable, multilevel decontamination and deodorization system of claim 10, further comprising a programming and status station microprocessor included in the programming and status station for managing a control panel and communications module also included with the programming and status station, wherein the control panel enables a user to set up and operate the decontamination station and the communications module enables remote monitoring of the decontamination station from outside a treatment area.

13. The portable, multilevel decontamination and deodorization system of claim 12, wherein said the programming and status station includes a rechargeable power source and electrical power and data connection to the environmental station during storage, said rechargeable power source configured to enable its operation and placement outside of the door of the treatment area.

14. The portable, multilevel decontamination and deodorization system of claim 12, wherein said the programming and status station is configured with warning indicia and lights and is further configured for placement outside a door of a treatment area to provide visual warnings about ongoing treatment and block entry to the treatment room.

15. A self-contained portable, multilevel decontamination and deodorization system restricted for use inside a room inside a building and capable of decontaminating and deodorizing the room at various levels within the overall height of the room starting from at least ten inches above ground level within the room to reach areas beneath furnishings that may exist in the room and reaching a defined limit above ground level within the room to reach above the furnishings that may exist in the room, comprising:
  a decontamination station having an upper, outer surface standing about ten inches from the ground during initial operation and including:
    a compartment configured to contain a chemical vessel, an air pressure vessel, and a telescoping chemical delivery tubing connected to the chemical and air pressure vessels and further including a media diffuser at its end, wherein the portable, multilevel decontamination and deodorization system is configured with the telescoping chemical delivery tubing to decontaminate a target environment at more than two vertical levels beginning from at least ten inches above the ground and reaching to a defined limit above ground level over a defined duration of time;
    an electromechanical module configured to control and cause incremental movement during the defined duration of time of telescoping chemical delivery tubing and a media diffuser located at the end of the telescoping tubing, upward and downward from the upper, outer surface, wherein operation of said electromechanical module is controlled by a decontamination station microprocessor;

a valve controller coupled to each of the chemical and pressure vessel to control flow of each into the telescoping chemical delivery tubing, wherein operation of said valve controller is controlled by the microprocessor;

environmental sensors configured to enable monitoring of treated environments; and a wireless communications module to enable communication between the decontamination station and a remote programming and status station; and a remote programming and status station to enable remote monitoring and control of the decontamination station from outside a treatment area, the remote programming and status station including:

a control panel and a remote programming and status station microprocessor to enable a user to remotely operate and monitor the decontamination station; and a wireless communications module to enable communication between the remote programming and status station and the decontamination station.

16. The portable, multilevel decontamination and deodorization system of claim 15, wherein said the programming and status station includes a rechargeable power source and electrical power and data connection to the environmental station during storage, said rechargeable power source configured to enable its operation and placement outside of the door of the treatment area.

17. The portable, multilevel decontamination and deodorization system of claim 15, wherein said the programming and status station is configured with warning indicia and lights and is further configured for placement outside a door of a treatment area to provide visual warnings about ongoing treatment and block entry to the treatment room.

18. The portable, multilevel decontamination and deodorization system of claim 15, said programming and status station and decontamination station each further comprising wireless communications to enable communication between the decontamination station and the programming and status station.

* * * * *